US011684257B2

(12) United States Patent
Levecq

(10) Patent No.: US 11,684,257 B2
(45) Date of Patent: Jun. 27, 2023

(54) SYSTEM AND METHOD FOR MULTI-SCALE RETINAL IMAGING

(71) Applicant: Imagine Eyes, Orsay (FR)

(72) Inventor: Xavier Levecq, Gif sur Yvette (FR)

(73) Assignee: Imagine Eyes, Orsay (FR)

( * ) Notice: Subject to any disclaimer, the term of this patent is extended or adjusted under 35 U.S.C. 154(b) by 811 days.

(21) Appl. No.: 16/608,393

(22) PCT Filed: Apr. 18, 2018

(86) PCT No.: PCT/EP2018/059854
§ 371 (c)(1),
(2) Date: Oct. 25, 2019

(87) PCT Pub. No.: WO2018/197288
PCT Pub. Date: Nov. 1, 2018

(65) Prior Publication Data
US 2020/0178797 A1 Jun. 11, 2020

(30) Foreign Application Priority Data

Apr. 25, 2017 (FR) ...................................... 1753568

(51) Int. Cl.
*A61B 3/02* (2006.01)
*A61B 3/113* (2006.01)
(Continued)

(52) U.S. Cl.
CPC .................. *A61B 3/14* (2013.01); *A61B 3/102* (2013.01); *A61B 3/1015* (2013.01);
(Continued)

(58) Field of Classification Search
CPC ......... A61B 3/02; A61B 3/102; A61B 3/1025; A61B 3/113; A61B 3/1015; A61B 3/103; A61B 3/1005; A61B 3/1225; A61B 3/024
(Continued)

(56) References Cited

U.S. PATENT DOCUMENTS 7,758,189 B2   7/2010   Hammer et al.
8,696,122 B2   4/2014   Hammer et al.
(Continued)

FOREIGN PATENT DOCUMENTS

FR   2970858 A1     8/2012
JP   2013517842 A   5/2013
(Continued)

OTHER PUBLICATIONS

International Search Report issued in International Application No. PCT/EP2018/059854, dated Jun. 14, 2018 (8 pages).
(Continued)

*Primary Examiner* — Dawayne Pinkney
(74) *Attorney, Agent, or Firm* — Osha Bergman Watanabe & Burton LLP

(57) ABSTRACT

The multi-scale scanning imaging system (200) of the retina comprises according to an example a lighting and detection module (210) configured for emitting a lighting beam and for detecting a beam reemitted by the retina, a first scanning module (231) of the lighting beam and the reemitted beam, a first optical path, referred to as a "wide field" path, and a second optical path, referred to as a "small field" path, for focusing the lighting beam on the retina and for receiving the beam reemitted by the retina. The "wide field" path comprises a first optical system (205, 201) configured to conjugate a plane located near a plane of rotation of the scanning module and the plane (17) of the entrance pupil of the eye (10). The "small field" path comprises a wavefront correction device (250), a second optical system (257, 256, 253) configured to conjugate a plane located near a plane of rotation of the at least one first scanning module and the effective surface of the wavefront correction device, a third optical system, comprising at least part of the first optical system, configured to conjugate said effective surface (251)
(Continued)

of the correction device and the plane of the entrance pupil of the eye. The multi-scale scanning imaging system further comprises a first optical deflection element (241) configured to send the beam reemitted by the retina on one and/or the other of the first and second imaging paths and intended to be positioned on the first imaging path, between the common part (201, 205) of the first and third optical systems and the scanning module (210), and on the second imaging path, between the common part of the first and third optical systems and the wavefront correction device.

14 Claims, 8 Drawing Sheets

(51) Int. Cl.
 *A61B 3/12* (2006.01)
 *A61B 3/14* (2006.01)
 *A61B 3/10* (2006.01)
 *G06T 7/00* (2017.01)
(52) U.S. Cl.
 CPC .......... *A61B 3/1025* (2013.01); *G06T 7/0012* (2013.01); *G06T 2207/30041* (2013.01)
(58) Field of Classification Search
 USPC ........ 351/206, 200, 205, 209–212, 221–223, 351/246
 See application file for complete search history.

(56) References Cited

U.S. PATENT DOCUMENTS

| | | | |
|---|---|---|---|
| 2007/0252951 A1* | 11/2007 | Hammer | ................. A61B 3/103 351/221 |
| 2017/0004344 A1* | 1/2017 | Nozato | ................. A61B 3/1025 |
| 2017/0206657 A1* | 7/2017 | Nozato | ..................... G06T 7/20 |

FOREIGN PATENT DOCUMENTS

| | | | |
|---|---|---|---|
| JP | 2014108212 A | | 6/2014 |
| JP | 2017018202 A | * | 1/2017 |
| WO | 2014053824 A1 | | 4/2014 |
| WO | 2016009603 A1 | | 1/2016 |

OTHER PUBLICATIONS

Written Opinion issued in International Application No. PCT/EP2018/059854; dated Jun. 14, 2018 (9 pages).
A. Roorda et al. "Adaptive optics scanning laser ophthalmoscopy" Optics Express, vol. 10, No. 9; May 6, 2002 (8 pages).
R. Zawadzki et al. "Adaptive-optics optical coherence tomography for high-resolution and high-speed 3D retinal in vivo imaging" Optics Express vol. 13, No. 21; Oct. 17, 2005 (15 pages).
A. Dubra et al. "First-order design of a reflective viewfinder for adaptive optics ophthalmoscopy" Optics Express vol. 20, No. 24; Nov. 19, 2012 (10 pages).
Office Action issued in Japanese Application No. 2019-558403; dated Mar. 8, 2022 (6 pages).

* cited by examiner

SYSTEM AND METHOD FOR MULTI-SCALE RETINAL IMAGING

PRIOR ART

Technical Field

This description relates to a multi-scale retinal imaging system and method, specifically a retinal scanning imaging system and method, for imaging simultaneously or successively fields of the retina of different sizes.

Prior Art

High-resolution imaging of the retina, that is to say at cellular level, allows early diagnosis of retinal diseases. The first effects of retinal diseases are known to affect the microscopic structures of the retina. The micro structures affected by the three most common and most serious retinal diseases (AMD for "Age-related Macular Degeneration", glaucoma, diabetic retinopathy) are the photoreceptors, among them the cones which have a size of between 2 and 5 µm, the micro vessels of the retina which are the smallest vessels of the human body (approximately 6 µm in diameter), and nerve cells which have a diameter of about 2 µm.

Several laboratories offer different imaging systems to obtain retinal imaging with cellular resolution. These systems, also called "ophthalmoscopes for adaptive optics" implement different modules for lighting and/or detecting the retina but all include an adaptive optics module for measuring the optical defects of the eye and the imaging system and for correcting the light rays coming from the retina and incident light rays on the detection system to gain resolution.

FIG. 1A shows a block diagram of a retinal imaging system based on the technology of ophthalmoscopy with adaptive optics laser scanning or AOSLO (abbreviation of the English expression Adaptive Optics Scanning Laser Ophthalmoscopy) as described for example in the article by A. Roorda et al. ("Adaptive optics scanning laser ophthalmoscopy" Optics Express 405, Vol. 10, No. 9, 2002). The assembly of the AOSLO primarily includes a lighting module 11 of the retina, a detection module 12, a scanning module 13, a correction module 14 comprising a correction plane for the incident light rays, a wavefront analysis module 15 and an imaging optical system 16. The lighting module comprises for example a laser diode coupled to an optical fibre to form a point source and an optical lens for forming, from the point source, a lighting beam. A diaphragm of the lighting module 11 defines a pupil. The lighting beam is sent, for example by a set of mirrors (not shown), on the correction module 14, for example a deformable mirror, then in the scanning module 13 to be directed so as to vertically and horizontally scan the eye 10 of a subject. The lighting beam is thus focused to form on the retina a quasi-point beam which scans the retina and the light that is for example backscattered by the retina, undergoes the same optical scanning to be sent to the deformable mirror 14 and the detection module 12, comprising for example a confocal detection hole and a detector which may be a photomultiplier or an avalanche photodiode. A set of optical elements symbolised by the imaging system 16 optically conjugates the retinal plane and the confocal detection hole of the detector. The analysis module of the wavefront 15 comprises for example a Shack-Hartmann type analyser; it receives the light backscattered by the retina and controls the deformable mirror to correct the lighting beam and the backscattered beam. The plane of the pupil of the lighting module, the plane of the deformable mirror and an analysis plane of the analysis module of the wavefront are optically conjugated with a predetermined plane 17 of the eye, for example the pupil plane of the eye.

FIG. 1B shows a block diagram of an OCT type of assembly (abbreviation of "Optical Coherence Tomography") coupled to adaptive optics. Such a system is described for example in R. Zawadzki ("Adaptive-optics optical coherence tomography for high resolution and high speed 3D retinal in vivo imaging" Optics Express 8532, Vol. 13, No. 21, 2005). OCT is based on the use of a low coherence interferometer. This imaging technique allows in vivo images of the tissue section, with a resolution of a few microns. The interest of OCT in ophthalmology comes from its ability to reveal in vivo tissue through other tissue scattering. The assembly of FIG. 1B represents in a very simplified form the main elements of an OCT type of assembly. We find a similar arrangement to that of AOSLO but wherein the detection module 12 is specific to OCT and includes an interferometer, for example a fibre interferometer, for example of the Michelson type. The entry point of the fibre (not shown) is conjugated with the retina of the eye 10 by means of an optical conjugation system symbolised by the lens 16. Compared with AOSLO, OCT technology provides a longitudinal section of the retina at the expense of the speed of acquisition.

However, the ophthalmoscopes with adaptive optics described above, whilst they exhibit excellent resolution, are limited to imaging a limited field of the retina, typically a field of a few degrees (less than 4°×4° normally); this is because the isoplanetism field of the eye does not allow a correction of aberrations on a much larger field with a simple adaptive optics system.

The article by A. Dubra et al. ("First-order design of a reflective viewfinder for adaptive optics ophthalmoscopy" Optics Express, Vol. 20, No. 24 (2012)) describes an adaptive optics ophthalmoscope of AOSLO type with a specific optical arrangement, in which a removable optical relay system permits toggling between a "small-field" mode having high resolution and a "wide-field" mode, with lower resolution. Therefore the establishment of the removable optical relay system allows you to switch to a "wide-field" optical arrangement with a larger angular magnification at the expense of a lower pupillary magnification. The wide-field mode allows a user to search the areas of interest of the retina. The removable optical relay system can then be removed to return to small-field mode for retinal imaging in high resolution.

In practice, such a system is however hardly possible for a commercial product. Indeed, the establishment of an optical relay system including a set of several optical conjugation elements needs one to readjust all optical settings, which is a delicate and often long operation, little suited to an inexperienced user.

The patent application WO 2016/009603 also describes a retinal imaging system of the AOSLO type suitable for small-field and wide-field imaging. More specifically, the disclosed system comprises two units adapted respectively to the low-resolution wide-field imaging and to the high resolution small-field imaging, the two units being separated by a beam splitter. Since each unit comprises a lighting and detection module, associated with a specific scanning module and its own imaging system, a user may have access to both the small-field and wide-field imaging without any adjustment and simultaneously. This system, however, requires doubling the lighting and detection modules and scanning modules for the formation of wide-field and small-field units, which is not satisfactory.

U.S. Pat. No. 7,758,189 describes a system for imaging the retina with a first wide-field unit of the LSLO type (for "line-scanning laser ophthalmoscope") and a second small-field unit of the AO-SDOCT type (for "Adaptive Optics Spectral Domain Optical Coherence Tomography"). In this patent, as in the application WO2016/009603 mentioned above, each unit includes a lighting and detection module associated with a specific scanning module, and its own imaging system.

One object of the present description is to provide a multi-scale scanning imaging system of the retina, that is to say adapted to a wide-field and small-field imaging that does not have the limitations of the prior art. Specifically, an object of this description is to provide a multi-scale retina scanning imaging system in which the small-field and wide-field imaging can be performed with the same lighting and detection module and the same scanning module, but can be used without difficulty by an inexperienced user.

SUMMARY OF THE INVENTION

In a first aspect, the present disclosure relates to a multi-scale scanning imaging system of the retina comprising:
- at least one first lighting and detection module configured for emitting at least one first lighting beam with a diameter of given dimension and for detecting at least one first beam reemitted by the retina;
- at least one first scanning module of the at least one first lighting beam and the at least one first reemitted beam;
- a first optical path, referred to as a "wide-field" path for focusing the at least one first lighting beam on the retina and for receiving the at least one first beam reemitted by the retina, comprising:
  - a first optical system with a first magnification, configured to conjugate a plane located near a plane of rotation of the at least one first scanning module and the plane of the entrance pupil of the eye;
- a second optical path, referred to as a "small-field" path for focusing the at least one first lighting beam on the retina and for receiving the at least one first beam reemitted by the retina, comprising:
  - a wavefront correction device having an effective surface of given dimension;
  - a second optical system with a second magnification configured to conjugate a plane located near a plane of rotation of the at least one first scanning module and the useful surface of the wavefront correction device,
  - a third optical system with a third magnification, comprising at least part of the first optical system configured to conjugate said useful surface of the correction device and the plane of the entrance pupil of the eye;
- at least one first optical deflection element, at least partially reflective, configured to send the at least one first beam reemitted by the retina on one and/or the other of the first and second imaging paths, and intended to be positioned on the first imaging path, between the common part of the first and third optical systems and the at least one first scanning module, and on the second imaging path, between the common part of the first and third optical systems and the wavefront correction device.

The Applicant has shown that this described imaging system enables small-field and/or wide-field imaging with a single lighting and detection module and a single scanning module for both paths, and is very easy to use. Indeed the particular arrangement of said first optical deflection element in the system can define the pupillary magnification specific to each path by fixed elements of the system. No adjustment of the optical elements with optical power is necessary when switching from one imaging path to another.

The said at least one first optical deflection element can be a simple removable reflecting surface, for example a removable mirror configured to switch between one and the other of the first and second imaging paths.

The said at least one first optical deflection element may also be a dichroic plate, configured to send the at least one first beam reemitted by the retina on one of said first and second imaging paths and to send at least one second beam reemitted by the retina, of a wavelength that is different from that of said at least one first beam reemitted by the retina, on the other imaging path. This configuration requires working with multiple beams of different wavelengths (and thus two sources and potentially two detectors in the lighting and detection module) but has the advantage of allowing simultaneous small-field and wide-field imaging with a single scanning module. The images in both the small-field and wide-field paths can therefore be carried out simultaneously by the same scanning module; they will have the same angular deflection, which makes colocation of the two images immediate.

According to one or more example embodiments, the first optical deflection element, for example a removable reflecting surface or a dichroic plate, is further configured to send the at least one first lighting beam on one and/or the other of the first and second imaging paths. In this case, only one optical deflection element is required in the imaging system, which makes it particularly simple to implement.

According one or more example embodiments, a second optical deflection element, for example a second removable reflecting surface or a dichroic plate, is configured to send the at least one first lighting beam on one and/or the other of the first and second imaging paths.

According to one or more example embodiments, said first lighting and detection module is configured for AOSLO type retinal imaging. Said first lighting and detection module in this example comprises at least one point light source and at least one confocal detection system.

According to one or more example embodiments, said first lighting and detection module is configured for OCT type retinal imaging. Said first lighting and detection module comprises at least one point light source and at least one interferometer for detection.

According to one or more example embodiments, the multi-scale scanning imaging system of the retina comprises a first lighting and detection module and a second lighting and detection module, each associated with a scanning module. For example, the first lighting and detection module is configured for AOSLO type retinal imaging and the second lighting and detection module is configured for OCT type retinal imaging, allowing it to benefit from two types of imaging, with the same system either in small-field or in wide-field mode.

According to one or more example embodiments, the scanning module is a two-dimensional scanning module for scanning in two different directions. The scanning module can also be a one-dimensional scanning module, for example in the case of the emission of a line of light carried out using a cylindrical lens for example and of reception by a strip of detectors.

Therefore, according to one or more example embodiments, the multi-scale scanning imaging system of the retina further comprises:
- a second lighting and detection module configured for emitting at least one second lighting beam with a diameter of given dimension and for detecting at least one second beam reemitted by the retina;
- a second scanning module of the at least one second lighting beam and the at least one second reemitted beam.

According to one or more example embodiments, the multi-scale scanning imaging system of the retina further comprises a wavefront analysis module configured to analyse at least part of the optical defects of a beam reemitted by the retina and sent on the second imaging path.

In the following description, the term "optical defects" are understood to be disturbance experienced by the light rays between the retina and a detector of a lighting or detection module. These defects comprise, for example defects introduced by the optical system of the eye but also by at least part of the optical field of the small-field imaging path.

According to one or more example embodiments, the wavefront analysis module comprises a Shack-Hartmann type analyser. Such a device allows the analysis, with respect to nominal directions, of the variation of the directions of the light rays after passing through the optical system marred with optical defects. Such a device performs this measurement by, for example, the arrangement of a matrix detector in the focal plane of a microlens array. Variations thus measured can be directly used for controlling the wavefront correction device.

According to one or more example embodiments, the multi-scale scanning imaging system further comprises a lighting module configured for emitting a retinal lighting beam for the measurement of the wavefront.

According to one or more example embodiments, the wavefront correction device includes a deformable mirror, a spatial modulator with liquid crystal light (SLM: "spatial light modulator"), a MEMS (micro electromechanical system), a multi-actuator liquid lens. The wavefront correction device can be controlled by a wavefront analysis module, for example in a slaving closed loop configuration, or be controlled by algorithms based on a quality criterion of the retinal images acquired by the lighting and detection module.

In a second aspect, the present disclosure relates to a method for imaging by scanning the retina by means of an imaging system under the first aspect.

According to one or more example embodiments, said at least one first optical deflection element is a removable reflecting surface and the method comprises removing said at least one first optical deflection element to switch from one of said first and second imaging paths to the other imaging path.

According to one or more example embodiments, said reflecting surface is inserted or removed according to a movement of insertion or withdrawal parallel to the reflecting surface; this prevents a positioning error when stopping the mirror from affecting the alignment of a beam reflected by said reflecting surface.

According to one or more example embodiments, the at least one first optical deflection element is a dichroic plate and the method comprises sending the at least one first beam reemitted by the retina on one of said first and second imaging paths and sending the at least one second beam reemitted by the retina on the other imaging path, said first and second beams reemitted by the retina having different wavelengths.

BRIEF DESCRIPTION OF THE FIGURES

Other advantages and features of the invention will appear on reading the description, illustrated by the following figures.

For consistency purposes, identical elements have been referred to by the same reference numerals in all the figures.

DETAILED DESCRIPTION

Figure 1A:
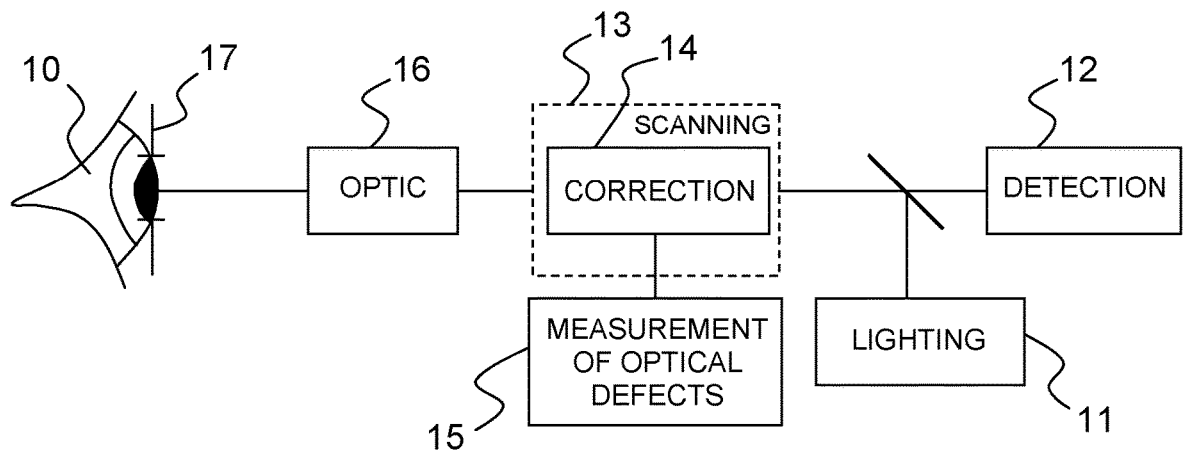
FIGS. 1A and 1B (already described) are block diagrams of scanning imaging systems of the retina known from the prior art.
Figure 1B:
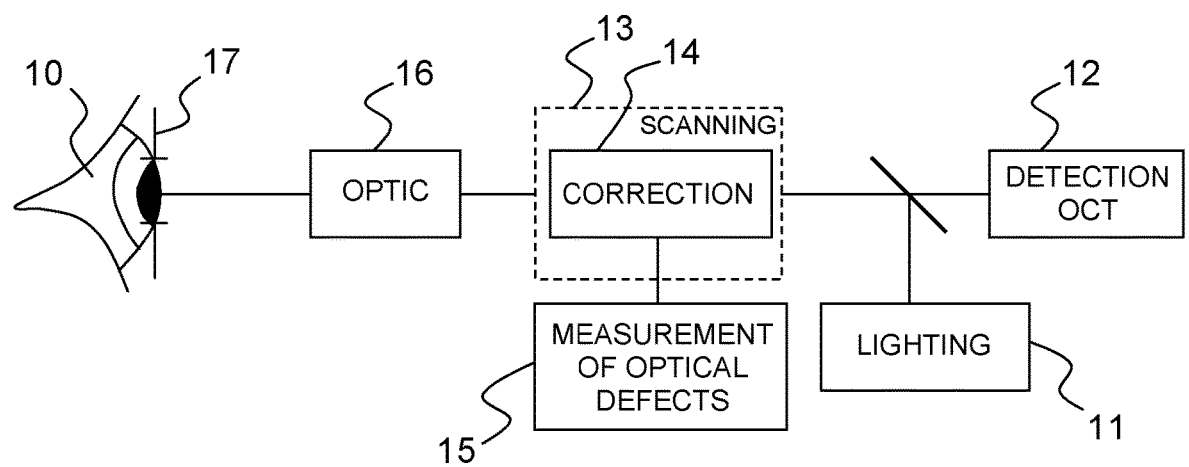
Figure 2A:
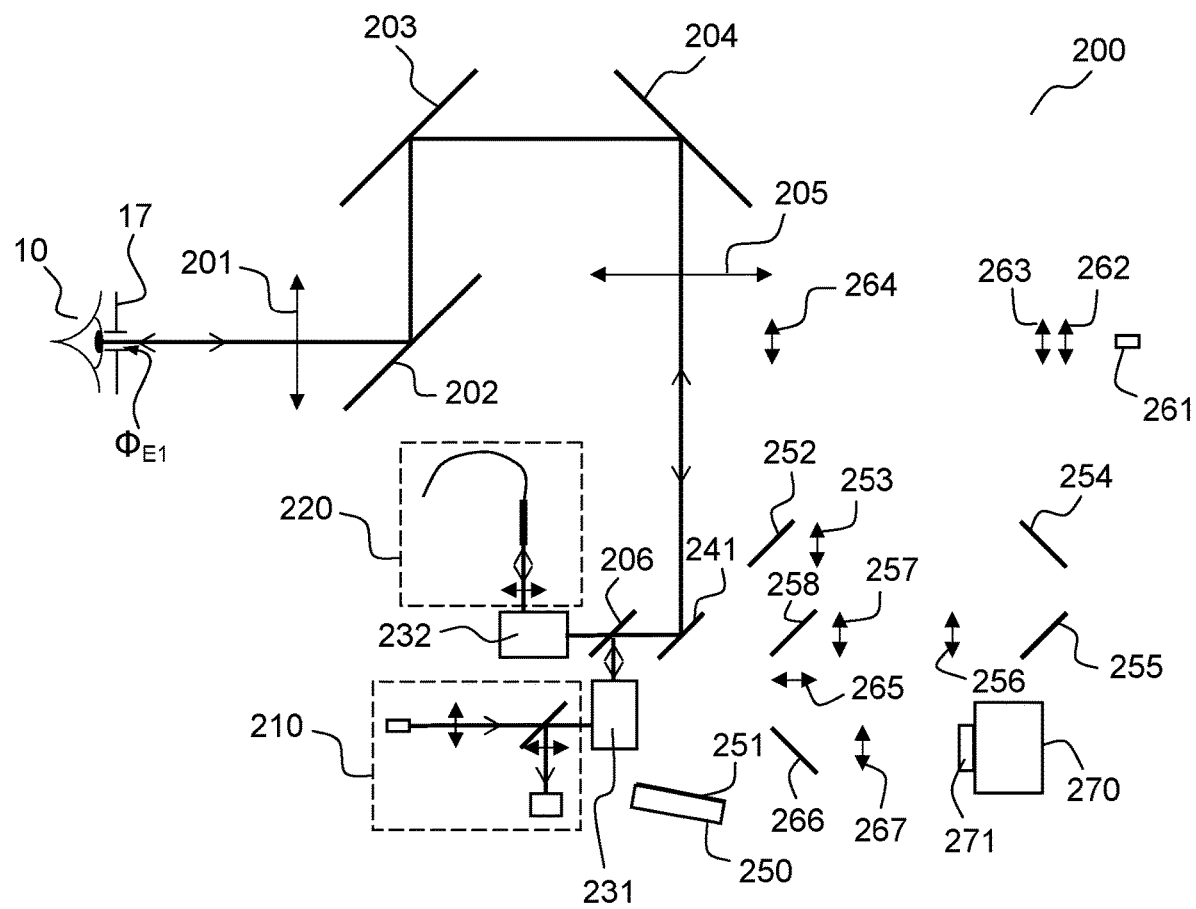
FIGS. 2A-2C are diagrams illustrating the operation of a first example embodiment of a scanning imaging system of the retina according to the present description.
Figure 2B:
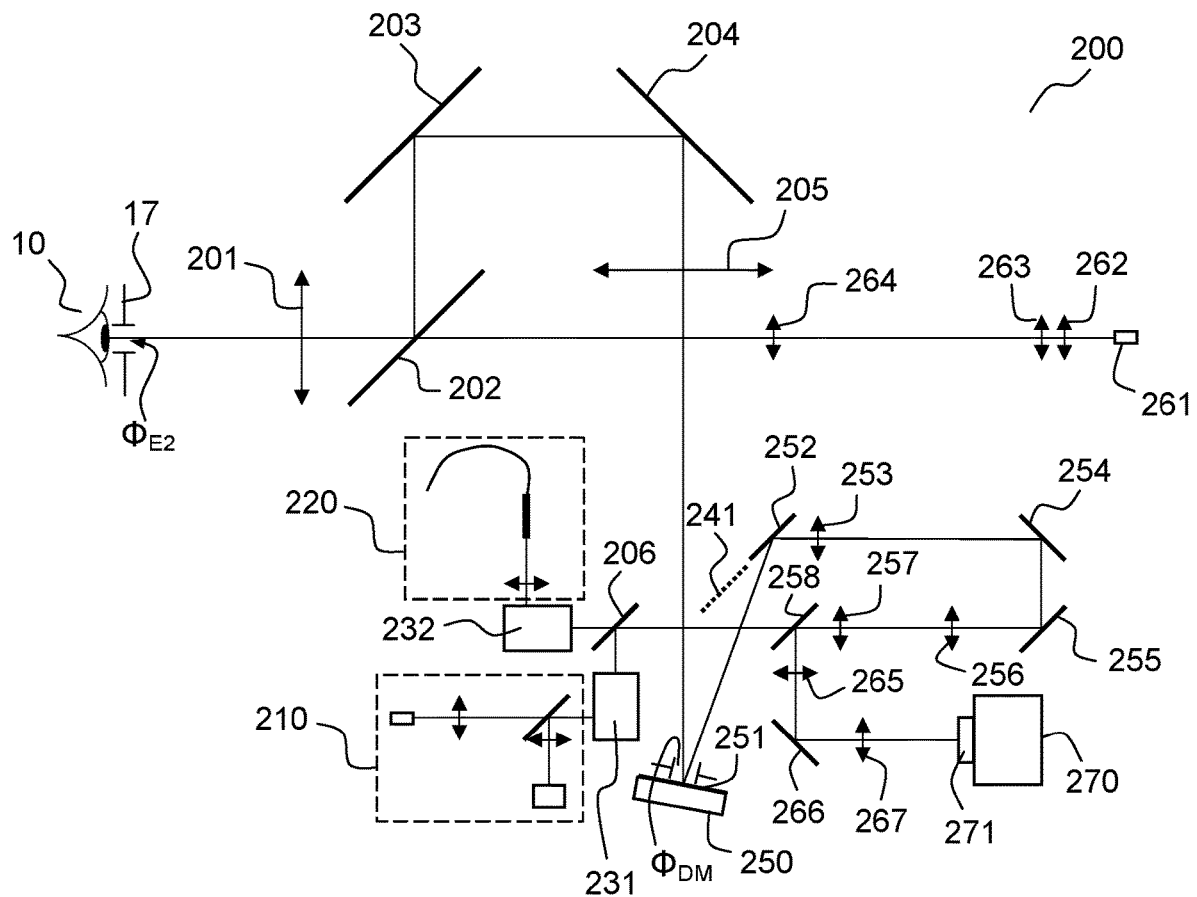
Figure 2C:
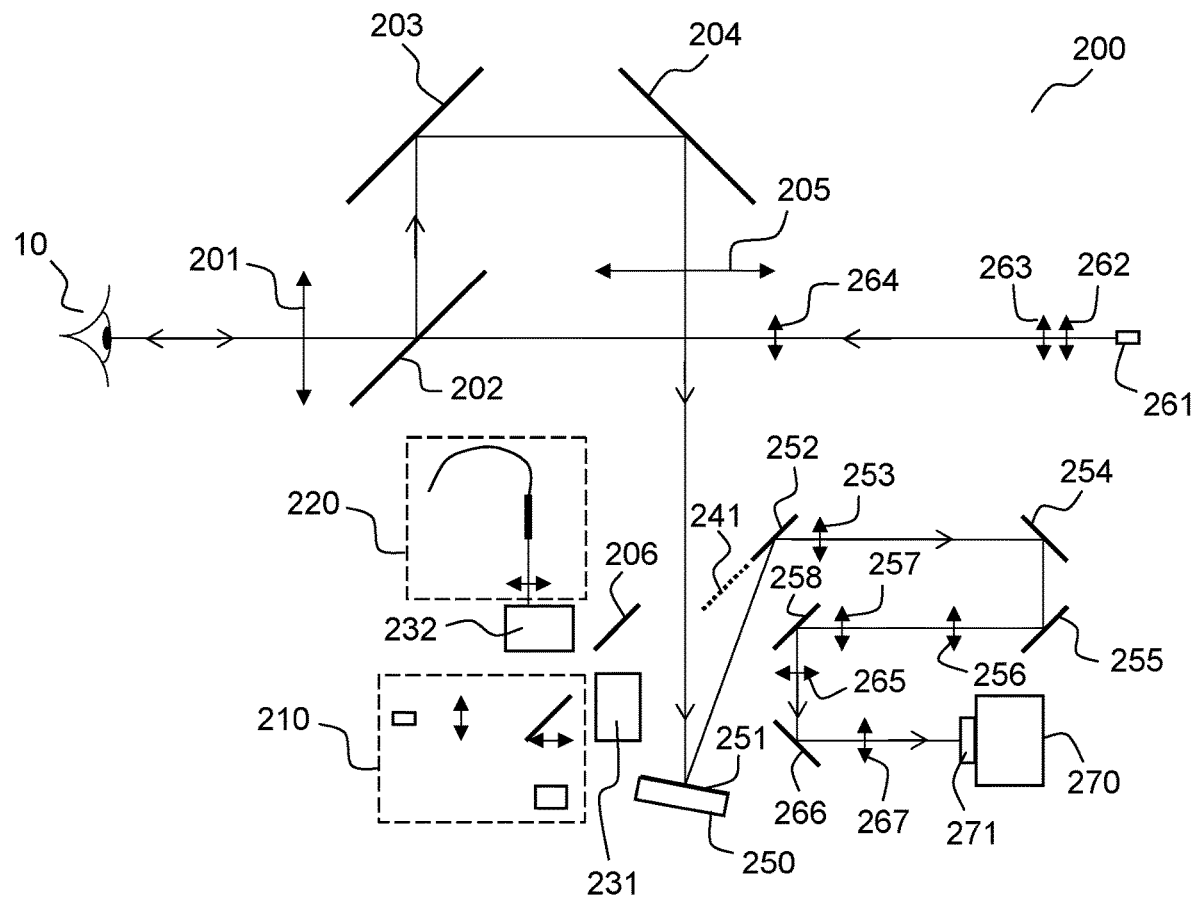

FIGS. 2A-2C illustrate the operation of a first example embodiment of a multi-scale scanning imaging system of the retina.

In this example, a single removable optical deflection element 241, e.g. a removable plane mirror reflecting at the wavelengths of the different lighting beams and beams reemitted by the retina, can switch between a wide-field imaging path (FIG. 2A) and a small-field imaging path (FIG. 2B). FIG. 2C illustrates the analysis of the optical defects in the case of small-field imaging.

The imaging system 200 shown in FIGS. 2A-2C comprises a first lighting and detection module 210 and a second lighting and detection module 220. Examples of such lighting and detection modules will be described in detail with reference to FIGS. 3A-3B. Each lighting and detection module is adapted for emitting one or more lighting beams and for detecting one or more beams reemitted by the retina after illumination by said lighting beams. A beam reemitted by the retina can be a backscattered beam at the same wavelength as the lighting beam, or be reemitted at a different wavelength when the lighting beam induces a fluorescence mechanism at the retina.

For example, a lighting and detection module may be adapted to the emission of two lighting beams of the retina at different wavelengths, as will be described later with reference to FIG. 4. Alternatively, as in the example of FIGS. 2A-2C, the lighting and detection modules are adapted for emitting a lighting beam at a given wavelength and for detecting a beam reemitted by the retina, at the same wavelength, or at a different wavelength in the case of fluorescence reemission by the retina.

The imaging system 200 further includes, associated with each of the lighting and detection modules 210, 220, a scanning module, for example adapted to two-dimensional scanning, respectively referenced as 231, 232.

Each scanning module is adapted for scanning the lighting beam emitted by the lighting and detection module and for scanning the beam reemitted by the retina to be sent to the lighting and detection module. A scanning module or "scanner" comprises, for example, a combination of motorised mirrors by means of galvanometric motors or a combination of a MEMS mirror (one axis) or a MEMS mirror with two axes. For each scanning module we can define a plane of rotation which comprises the rotational axis; a plane of rotation is then merged with the plane of the mirror. In the case of using two separate mirrors to achieve the two rotations, it is advantageous that the planes of rotation of the two mirrors are optically conjugated, for example by means of an optical system which conjugates the two planes. In the case where the scanning module is a two-dimensional scanning module comprising two separate scanning mirrors that are not conjugated, it is advantageous that they are situated at the shortest possible distance from one another.

In the example of FIGS. 2A-2C, the lighting beams respectively emitted by the lighting and detection modules 210, 220 and scanned by the scanning modules 231 and 232, respectively, are combined and sent to the imaging paths by means of a partially reflecting plate 206, for example a dichroic plate if the lighting beams have different wavelengths. The same partially reflecting plate separates the beams reemitted by the retina to each of the lighting and detection modules.

The imaging system 200 comprises according to the present disclosure a first optical path, referred to as a "wide-field" path, and a second optical path, referred to as a "small-field" path, one or the other of these paths can be enabled, in the example of FIGS. 2A-2C, through the introduction or removal of the removable reflecting surface 241; and each of said paths allows the lighting beam coming from the lighting and detection module to be focused on the retina and the beam reemitted by the retina to be received.

FIG. 2A shows the case where the wide-field path is enabled. To do this in this example, the removable reflecting surface 241 is established. Since it can be a simple mirror, for example a plane mirror, no adjustment becomes necessary. For example, the mirror is inserted by an insertion movement parallel to the reflecting surface, thus preventing a positioning error during the mirror stop from affecting the alignment of a beam reflected by said reflecting surface.

The wide-field path comprises a first optical system, comprising in this example a set of optical elements 201, 205, and having a first magnification $g_1$. The first optical system is intended to conjugate a plane positioned near a plane of rotation of the scanning module and the plane 17 of the entrance pupil of the eye 10 of a patient.

In the case where the scanning module comprises a mirror with a plane of rotation, or two mirrors optically conjugated with each other, the first optical system can conjugate the or one of said planes of rotation with the plane 17 of the entrance pupil of the eye 10. In the case where the scanning module is a two-dimensional scanning module comprising two separate and non-conjugated scanning mirrors, the first optical system may conjugate a plane between the two mirrors, for example a plane located at a median distance from the two mirrors with the plane 17 of the entrance pupil of the eye 10.

The wide-field path further comprises a set of optical deflection elements, in this example 204, 203, 202 for directing the lighting beam towards the eye 10.

Thus, in the case of "wide field" imaging, the diameter $\phi_{E1}$ of the exit pupil of the optical imaging system in plane 17 of the pupil of the eye is given by:

$$\phi_{E1} = g_1 \phi_{ecl} \quad (1)$$

The "optical imaging system" is defined by the set of imaging elements between the entrance pupil of the eye and a detector of a lighting and detection module and $\phi_{ecl}$ is the diameter of the lighting beam output from the scanning module.

Note that if there are two lighting and detection modules, there may be different diameters of lighting beams and therefore different $\phi_{E1}$ values, although this difference should be minimised.

The term "pupil" of an optical system is the smaller opening which limits the input or the propagation of light rays in the system. This opening may be actual in the case where a physical diaphragm, pupil of the optical system considered, limits the entry of light or virtual rays, in the case where this opening is an image of the physical pupil of the optical system which is within the optical system and which is formed for example by a diaphragm. Thus, in the case where the exit pupil of the imaging optical system is positioned in the pupil plane of the eye or in a plane lying near the latter, this exit pupil is a virtual image of a physical diaphragm located within said imaging optical system.

FIG. 2B shows the case where the small-field path is enabled. To do this in this example, the removable reflecting surface 241 is removed.

The "small field" path includes a wavefront correction device 250 having an effective surface 251 of given dimension, a second optical system used for conjugating a plane located near a plane of rotation of the scanning module and the working surface 251 and having a second magnification $g_2$. The second optical system comprises in the example of FIGS. 2A-2C a set of optical elements 257, 256, 253.

As for the wide-field path, in the case where the scanning module comprises a mirror with a plane of rotation, or two mirrors optically conjugated with each other, the second optical system may conjugate the or one of said planes of rotation with the useful surface 251 of the wavefront correction device. In the case where the scanning module is a two-dimensional scanning module comprising two separate and non-conjugated scanning mirrors, the second optical system may conjugate a plane between the two mirrors, for example a plane located at a median distance from the two mirrors with the useful surface 251 of the front correction device.

The "small field" path further comprises a third optical system adapted to conjugate the effective surface 251 of the correcting device and the plane 17 of the entrance pupil of the eye 10, having a third magnification $g_3$. The third optical system comprises at least part of the first optical system; in the example of FIGS. 2A-2C, the third optical system comprises all the optical elements of the first optical system, namely the optical elements 205, 201; the third optical system is thus coincident with the first optical system ($g_3 = g_1$).

The small field path further comprises a set of optical deflection elements, in this example 255, 254, 252, for directing the lighting beam towards the eye 10 of a patient.

Thus, in the case of "small-field" imaging, the diameter $\phi_{E2}$ of the exit pupil of the optical imaging system in the plane 17 of the pupil of the eye, is given by:

$$\phi_{E2} = g_3 \phi_{DM} \quad (2)$$

Where $\phi_{DM}$ is the smaller of the two diameters between the diameter of the lighting surface of the wavefront correction device and the diameter of the effective surface of the wavefront correction device, and satisfies:

$$\phi_{DM} = g_2 \phi_{ecl} \quad (3)$$

In general, for a system sized to optimise resolution, $\phi_{DM}$ is the diameter of the effective surface of the wavefront correction device.

Thus, the result is the following magnification between the diameter of the lighting beam output from the scanning module and the diameter $\phi_{E2}$ of the exit pupil of the optical imaging system in the plane 17 of the pupil of the eye:

$$\phi_{E2} = g_3 \cdot g_2 \phi_{ecl} \quad (4)$$

From equations (1) and (4), we see that it is thus possible to change the dimension of the diameter of the exit pupil of the imaging optical system in the plane 17 of the pupil of the eye by a simple introduction or withdrawal of the reflecting surface 241.

With a larger pupil (FIG. 2B), for the same scanning angle at the level of the one or more scanning mirrors, the field becomes smaller but the resolution is higher. Indeed, the resolution limit is directly proportional to the size of the pupil. On the other hand, the scanning angle at the entrance pupil of the eye is equal to the scanning angle at the one or more scanning mirrors multiplied by the magnification of the optical system between the one or more scanning mirrors and the entrance pupil in the eye. However, the enlargement is the inverse of the magnification. Therefore if the entrance pupil is larger by a factor X in the case of small-field imaging relative to the entrance pupil in the eye of the case of wide-field imaging, the scanning angle at the entrance pupil into the eye for the small-field imaging is smaller by the same factor X than the scanning angle at the entrance pupil into the eye for wide-field imaging (for the same physical scanning angle of the one or more scanning mirrors). A reduction of the scanning angle at the entrance pupil in the eye for small-field imaging is quite acceptable because when seeking higher resolution (case of small-field imaging), the isoplanetism field of the eye still reduces the image field to some degree (typically 4°×4°).

In the example of FIGS. 2A-2C, the imaging system 200 further comprises a wavefront analysis module adapted for the analysis of optical defects of a beam reemitted by the retina and sent on the second imaging path. FIG. 2C illustrates more specifically the path of the optical beams for the analysis of the optical defects (analysis path).

This involves analysing disturbances experienced by light rays between the retina and a detector of the lighting and detection module, and more specifically, between the retina and a plane of analysis of the wavefront analyser. Optical defects within the meaning of this disclosure thus comprise the defects introduced by the optical system of the eye but also by the part of the optical imaging system that is common with the analysis path. Note however that any defects of the analysis path could have been measured during manufacture and the correction can take this into account. The wavefront analysis module includes, for example, an analyser 270 of the Shack-Hartmann type (HASO®32-eye Imagine Eyes®), comprising an analysis plane 271 formed by a set of micro lenses and a detector placed in the focal plane of the microlenses.

In the example in FIGS. 2A-2C, a partially reflecting blade 258 allows the collection of a beam reemitted by the retina to send it to the wavefront analysis module. The optical defects module in this example includes a set of optical elements 265, 267 allowing the conjugation of the analysis plane 271 with the plane 17 of the imaging system entrance pupil as well as a deflection mirror 266. According to an example embodiment, the blade 258 is a dichroic plate and the analysis beam has a different wavelength from the one or more other beams reemitted by the retina for imaging, as described subsequently.

A computer (not shown) determines the optical defects of the system and sends a correction command to the correcting device 250, for example a deformable mirror of the Mirao 52-e Imagine Eyes® type. It will be an advantage to have the computer associated with the Shack-Hartmann determine, relative to nominal directions, the variation in the directions of the light rays after passing through the optical system marred by optical defects. The thus measured variations can be directly exploited for the control of the deformable mirror. The deformable mirror plane is also optically conjugated with the plane 17 of the imaging system entrance pupil.

Other wavefront correction devices may be used, such as a spatial modulator with liquid crystal light (SLM or "spatial light modulator") or a MEMs or a multi-actuator liquid lens.

In the example of FIGS. 2A-2C, the multi-scale scanning imaging system further includes a lighting module adapted for emitting a lighting beam of the retina for the measurement of the optical defects.

The lighting module comprises in this example a source 261 for lighting the retina for the analysis of the optical defects of the imaging system. The source 261 can form a secondary source point on the retina of the eye of the subject. For example, the centre wavelength of the lighting source 261 for the analysis of the optical defects is 750 nm, such a wavelength being comfortable for the subject, and as close as possible to the one or more imaging wavelength(s). Preferably, the wavelength of the source 261 is different from that of the light sources of the lighting and detection modules 210, 220 in order to separate the optical paths between the measurement of the optical defects and imaging of the retina. The source 261 is for example a laser diode or more advantageously an SLED super luminescent diode. A beam splitter 202 is used to send to the eye 10 of the subject the light beams for lighting the retina for imaging and for the analysis of the optical defects. A set of optical elements 262, 263, 264 make it possible to form, from the light source 261, a beam to be focused on the retina. The lens 263 can be a liquid lens at variable power (Varioptic® Artic® 25H0 type for example) to compensate for the refractive error of the examined eye.

Figure 3A:
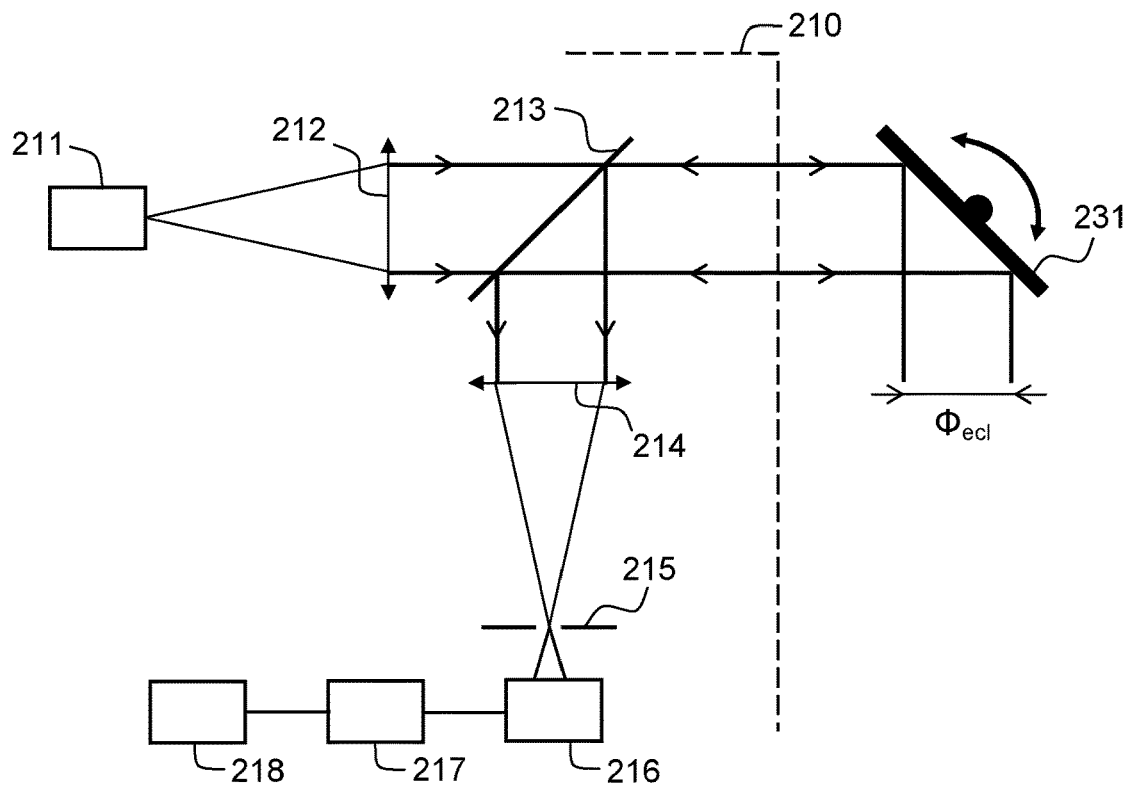
FIGS. 3A, 3B are diagrams showing examples of lighting and detection modules, suitable respectively for the AOSLO and OCT type imaging of the retina.
Figure 3B:
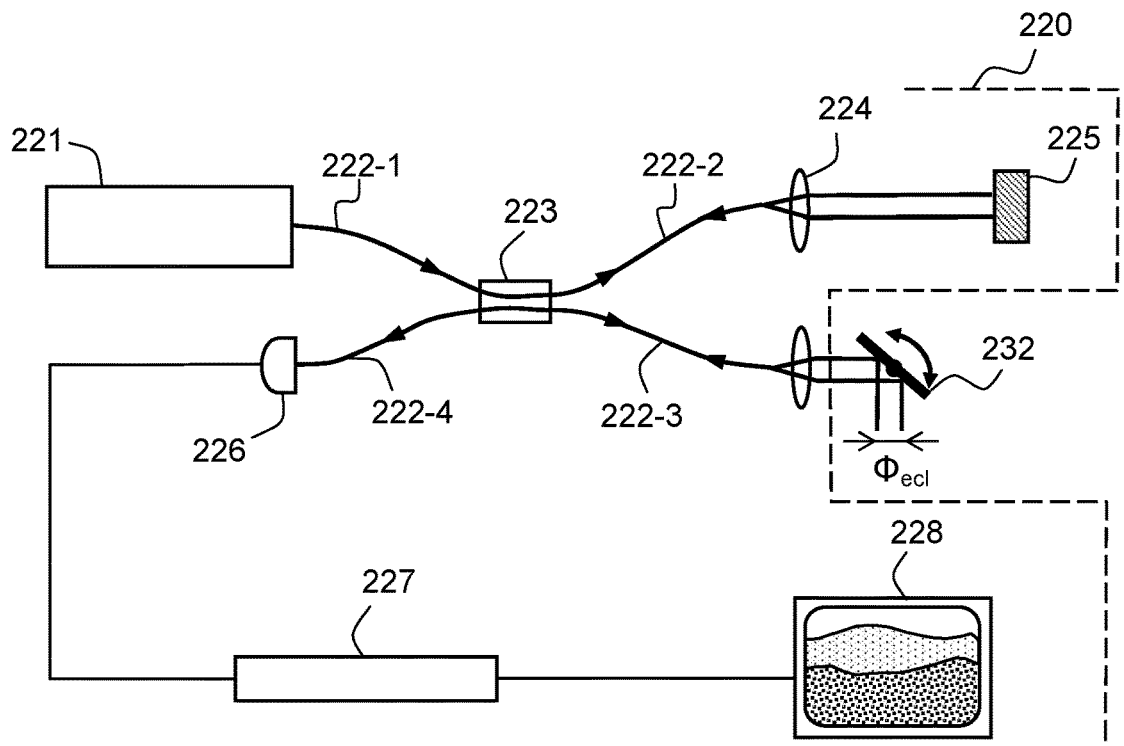

FIGS. 3A and 3B show examples of lighting and detection modules, respectively suitable for AOSLO type and OCT type imaging of the retina.

FIG. 3A shows a lighting and detection module 210 of a known type, suitable for AOSLO type imaging of the retina respectively, and a scanning module 231 for scanning a lighting beam emitted by the module 210 and a beam reemitted by the retina after illumination by said lighting beam. The module 210 comprises in this example a light source 211, for example a laser diode coupled to an optical fibre to form a source point and an optical lens 212 for forming from the source point a lighting beam of a given diameter $\phi_{ecl}$. The lighting and detection module 210 further comprises a confocal detection hole 215 through which is focused, using an optical element 214, the beam reemitted by the retina and returned to the module 210. The module 210 further comprises a detector 216, e.g. a photomultiplier or an avalanche photodiode, connected to a signal processing unit 217, itself connected to a display 218. A partially reflecting plate 213 separates the beams at emission and at reception.

FIG. 3B shows a lighting and detection module 220 of a known type, suitable for OCT type imaging of the retina respectively, and a scanning module 232 for scanning a lighting beam emitted by the module 220 and a beam reemitted by the retina after illumination by said lighting beam. The module 220 comprises in this example a light source 221 with low temporal coherence, such as a light source of the SLED type and a detection module formed by an interferometer, for example a fibre interferometer, for example of the Michelson type, comprising in this example, a fibre reference arm with a reflection element 225 and an optic 224. A coupler 223 receives the beams from the fibres 222-1, 222-2, 222-3 respectively from the source, of the reference arm and the retina to form interference on a detector 226, for example a photomultiplier or an avalanche photodiode; the module 220 further includes a signal processing unit 227, itself connected to a display 228.

Figure 4:
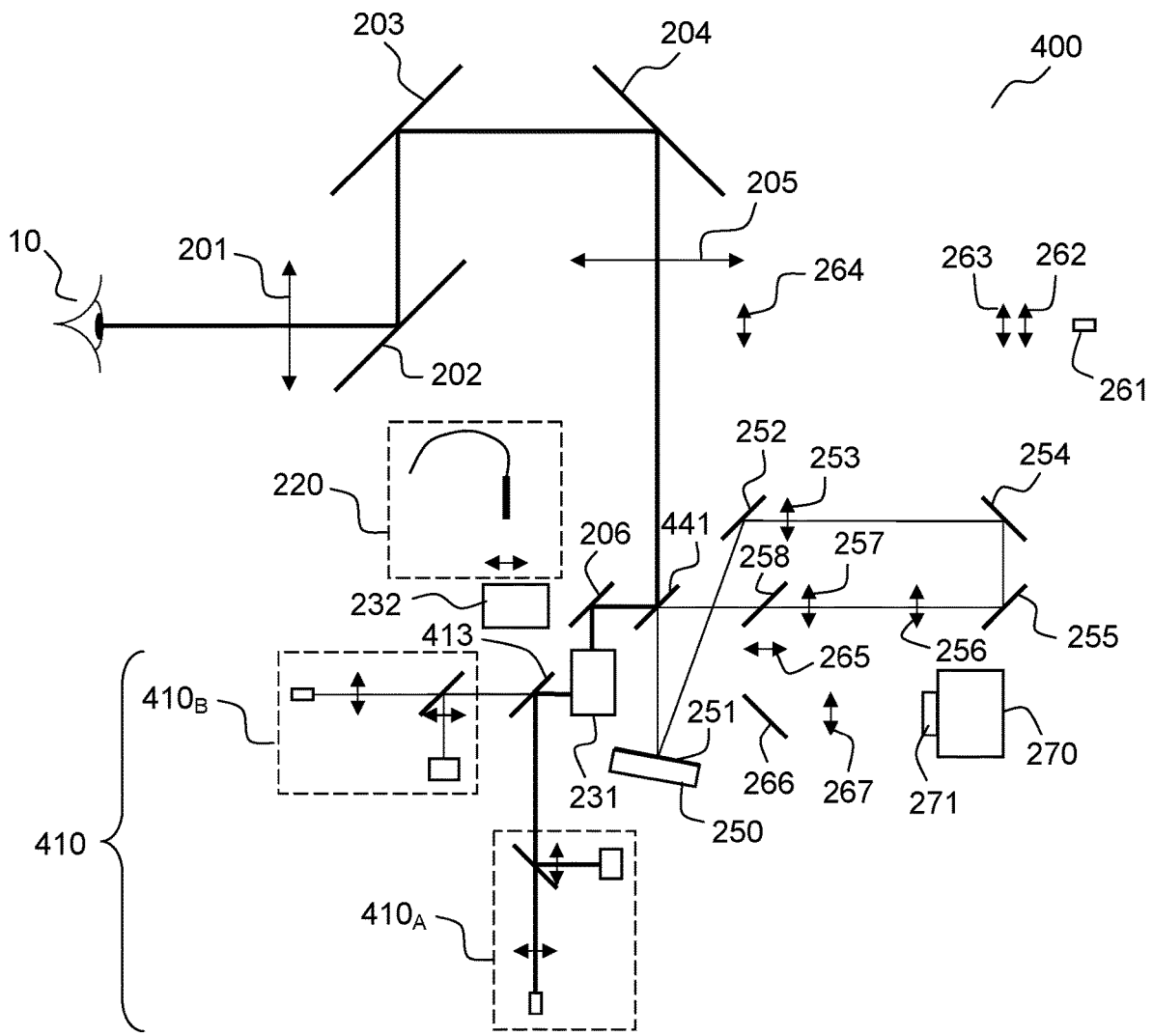
FIG. 4 is a diagram showing the operation of another example embodiment of a scanning imaging system of the retina according to the present description.

FIG. 4 illustrates a diagram of the operation of another example embodiment of a scanning imaging system 400 of the retina according to the present description.

In this example, the optical deflection element for separating the small-field and wide-field paths is not a removable reflecting surface but a dichroic plate 441. All the elements identical to those described with reference to FIGS. 2A-2C are indicated with identical reference numerals and are not described again.

To facilitate understanding of the figure, it is assumed in this example that only a lighting and detection module 410 is active, for example a lighting and detection module adapted to AOSLO type imaging of the retina respectively.

In this example, the lighting and detection module 410 comprises a sub-module $410_A$ for lighting and detection at a first wavelength and sub-module 4108 for lighting and detection at a second wavelength, different from the first wavelength.

In this example, the lighting beam at the first wavelength, illustrated by a bold line, and emitted by the sub-module $410_A$, is scanned by the scanning module 231 and then directly reflected on the wide-field path comprising the first optical system 205, 201 using the dichroic plate 441.

The lighting beam at the second wavelength, as shown by a thin line, and emitted by the sub-module $410_B$, is also scanned by the scanning module 231 and then transmitted using the dichroic plate 441 towards the small field path comprising the second (257, 256, 253) and third (205, 201) optical systems.

A partially reflecting mirror 413 allows lighting beams to be sent to the retina of the eye and the beams reemitted by the illuminated retina respectively to be sent to each of the sub-modules.

This configuration allows for simultaneous access to the small field and wide-field imaging paths with the same scanning module 231 and thereby allows a very easy and reliable colocation of the two images. The relationship between the angular size of the two fields equals the ratio between the sizes of the diameters of the pupils of the two beams at the level of the pupil of the eye.

Figure 5A:
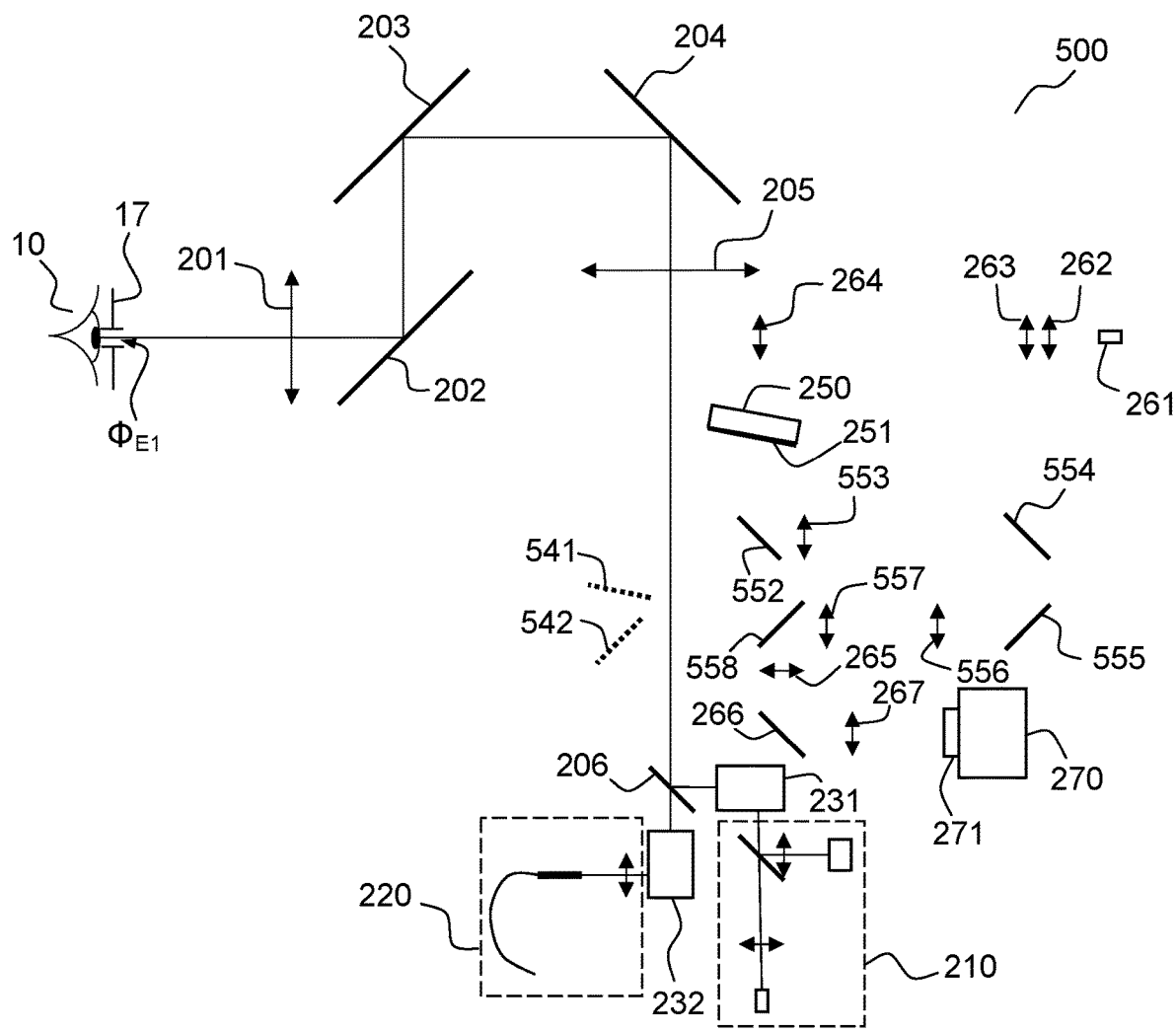
FIGS. 5A-5B are diagrams illustrating the operation of another example embodiment of a scanning imaging system of the retina according to the present description.
Figure 5B:
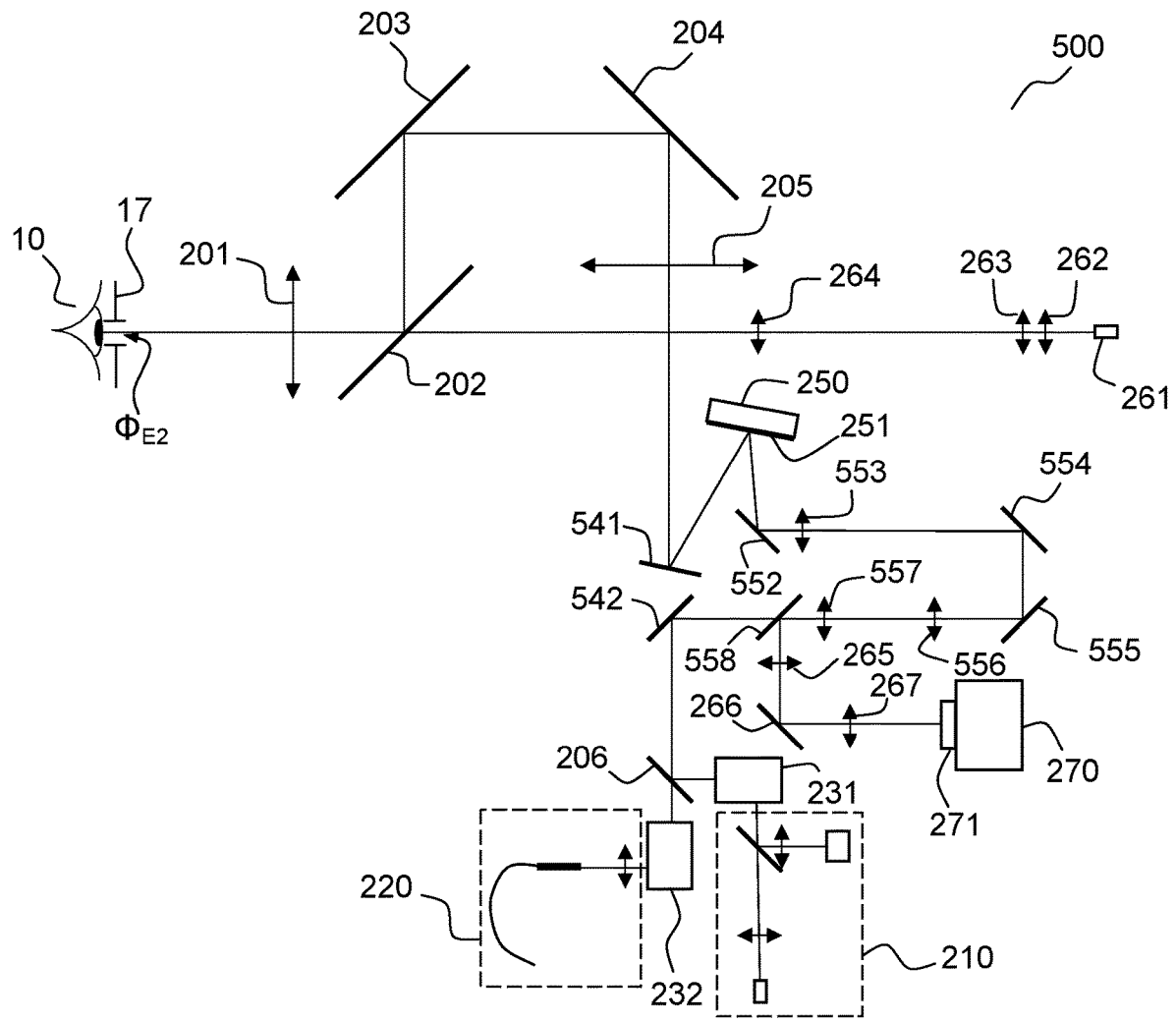

FIGS. 5A-5B illustrate the operation of another example embodiment of a scanning imaging system of the retina 500 of the present disclosure.

In this example, a first optical deflection element 541, at least partially reflecting, allows a first beam reemitted by the retina to be sent on one and/or the other of the first and second imaging paths, and a second optical deflection element 542 allows the at least one first lighting beam to be sent on one and/or the other of the first and second imaging paths.

Again, all elements identical to those described with reference to FIGS. 2A-2C are indicated with identical reference numerals and are not described again.

For example, the first and second optical deflection elements 541, 542 are connected removable reflecting surfaces. Alternatively, the first and second optical deflection elements 541, 542 may be dichroic plates as previously described with reference to FIG. 4.

Thus, the FIG. 5A illustrates the operation of the imaging system of the retina when the wide-field optical path is enabled, with the first optical system 205, 201, which in this example is obtained when the deflecting elements 541, 542 are removed. FIG. 5B illustrates the operation of the imaging system of the retina when the small field optical path is enabled, which in this example is obtained when the deflecting elements 541, 542 are set up. This particular configuration allows indeed the number of reflective elements in the wide-field path to be limited.

The "small field" path comprises, as before, a wavefront correction device 250 having an effective surface 251 of a given dimension, and a second optical system for conjugating a plane of rotation of the scanning module and the effective surface 251 and having a second magnification $g_2$. The second optical system includes in the example of FIGS. 5A-5B a set of optical elements 557, 556, 553. The "small field" path further includes, as before, a third optical system adapted to conjugate the effective surface 251 of the correcting device and the plane 17 of the entrance pupil of the eye 10, having a third magnification $g_3$. The third optical system comprises in this example the optical elements 205, 201 forming the first optical system. The small field path further comprises a set of optical deflection elements, in this example 555, 554, 552, for directing the lighting beam towards the eye 10 of a patient. A partially-reflecting plate 558, for example a dichroic plate, allows as above the beam reemitted by the retina to be deflected at the wavelength of the analysis source 261 to the optical defects analysis module.

Although described through a number of detailed example embodiments, the retinal imaging device and the method according to the invention include various variations, modifications and improvements which will become apparent to those skilled in the art, it being understood that these variations, modifications and improvements are part of the scope of the invention as defined by the following claims.

In particular, a single lighting and detection module can be used, in which case the partially reflecting plate 206 illustrated in FIGS. 2A-2C, 4, 5A-5B is no longer necessary. Furthermore, examples of the scanning imaging systems of the retina have been described with a lighting and detection module adapted to retinal imaging of the AOSLO or OCT type. The present disclosure is generally applicable to any imaging device by scanning of the retina with adaptive optics.

The lighting module of the retina for optical defects analysis is optional, whereby defects analysis can be performed on a beam reemitted by the retina, resulting from the lighting by one of the lighting and detection modules 210, 220. It is also possible to dispense with a wavefront analysis module, for example by implementing a correction method which is based on a criterion regarding the quality of the images acquired, although the use of a wavefront analysis module is preferred for reasons of slaving speed.

Moreover, the optical systems are shown for illustrative purposes and may be changed depending on the specific needs of the application; e.g. the refractive optical systems can be replaced with reflective optical systems.

Also, in the example of FIGS. 2A-2C, the "wide-field" imaging path is enabled when the one or more deflection elements are set up and the "small field" imaging path is enabled when the one or more deflection elements are removed but the optical system could easily be designed such that the reverse applies (as in the case of FIGS. 5A-5B).

The invention claimed is:

1. A multi-scale scanning imaging system of a retina of an eye comprising:
a first lighting and detection module configured for emitting a first lighting beam with a diameter of given dimension and for detecting a first reemitted beam corresponding to a first beam reemitted by the retina;
a first scanning module of the first lighting beam and the first reemitted beam;
a first optical path for a "wide field" path and for focusing the first lighting beam on the retina and for receiving the first beam reemitted by the retina, comprising:
a first optical system with a first magnification configured to conjugate a plane located near a plane of rotation of the first scanning module and a plane of an entrance pupil of the eye;
a second optical path for a "small field" path and for focusing the first lighting beam on the retina and for receiving the first beam reemitted by the retina, comprising:
a wavefront correction device having an effective surface of given dimension;
a second optical system with a second magnification configured to conjugate a plane located near a plane of rotation of the first scanning module and the effective surface of the wavefront correction device,
a third optical system with a third magnification, comprising at least part of the first optical system and configured to conjugate the effective surface of the wavefront correction device and the plane of the entrance pupil of the eye;
a first optical deflection element, at least partially reflective, configured to send the first beam reemitted by the retina on a first imaging path and/or a second imaging path,
wherein the first optical deflection element is intended to be positioned on the first imaging path, between a common part of the first optical system and third optical system and the first scanning module, and on the second imaging path, between a common part of the first optical system and the third optical system and the wavefront correction device.

2. The multi-scale scanning imaging system according to claim 1, wherein the first optical deflection element is further configured to send the at least one first lighting beam on the first imaging path and/or the second imaging path.

3. The multi-scale scanning imaging system according to claim 1, wherein a second optical deflection element is configured to send the first lighting beam on the first imaging path and the second imaging path.

4. The multi-scale scanning imaging system according to claim 1, wherein the first optical deflection element is a removable reflecting surface configured to switch between the first imaging path and the second imaging path.

5. The multi-scale scanning imaging system according to claim 1, wherein the first optical deflection element is a dichroic plate, configured to send the first beam reemitted by the retina on one of the first imaging path and the second imaging path and sending a second beam reemitted by the retina, of a wavelength that it different from that of the first beam reemitted by the retina, on the other imaging path.

6. The multi-scale scanning imaging system according to claim 1, wherein the first lighting and detection module comprises a point light source and a confocal detection system and is configured for AOSLO type imaging of the retina.

7. The multi-scale scanning imaging system according to claim 1, wherein the first lighting and detection module comprises a point light source and an interferometer and is configured for OCT type imaging of the retina.

8. The multi-scale scanning imaging system according to claim 1, further comprising:
a second lighting and detection module configured for emitting a second lighting beam with a diameter of given dimension and for detecting a second reemitted beam corresponding to a second beam reemitted by the retina; and
a second scanning module of the second lighting beam and the second reemitted beam.

9. The multi-scale scanning imaging system according to claim 1, further comprising a wavefront analysis module configured to analyse at least part of optical defects of a second beam reemitted by the retina and sent on the second imaging path.

10. The multi-scale scanning imaging system according to claim 9, wherein the wavefront analysis module comprises a Shack-Hartmann type analyser.

11. The multi-scale scanning imaging system according to claim 9, further comprising a lighting module configured for emitting a lighting beam for lighting the retina for a measurement of the optical defects.

12. A scanning imaging method of the retina using the multi-scale scanning imaging system according to claim 9.

13. The scanning imaging method of the retina according to claim 12, wherein the first optical deflection element is a removable reflecting surface, and wherein the scanning imaging method comprises:
removing the first optical deflection element to switch from one of the first imaging path and the second imaging path to the other imaging path.

14. The scanning imaging method of the retina according to claim 12, wherein the first optical deflection element is a dichroic plate, and wherein the scanning imaging method comprises:
sending the first beam reemitted by the retina on one of the first imaging path and the second imaging path and sending a second beam reemitted by the retina on the other imaging path, the first beam and the second beam reemitted by the retina having different wavelengths.

* * * * *